(12) United States Patent
Markowitz et al.

(10) Patent No.: US 7,941,213 B2
(45) Date of Patent: May 10, 2011

(54) SYSTEM AND METHOD TO EVALUATE ELECTRODE POSITION AND SPACING

(75) Inventors: H. Toby Markowitz, Roseville, MN (US); Phillip Falkner, Minneapolis, MN (US); Douglas A. Hettrick, Andover, MN (US); Sameh Sowelam, Fridley, MN (US)

(73) Assignee: Medtronic, Inc., Minneapolis, MN (US)

( * ) Notice: Subject to any disclaimer, the term of this patent is extended or adjusted under 35 U.S.C. 154(b) by 303 days.

(21) Appl. No.: 12/183,796

(22) Filed: Jul. 31, 2008

(65) Prior Publication Data

US 2009/0093857 A1 Apr. 9, 2009

Related U.S. Application Data

(63) Continuation-in-part of application No. 11/966,382, filed on Dec. 28, 2007, now abandoned.

(60) Provisional application No. 60/912,610, filed on Apr. 18, 2007, provisional application No. 60/882,420, filed on Dec. 28, 2006, provisional application No. 60/882,431, filed on Dec. 28, 2006, provisional application No. 60/882,435, filed on Dec. 28, 2006, provisional application No. 60/882,428, filed on Dec. 28, 2006, provisional application No. 60/882,430, filed on Dec. 28, 2006, provisional application No. 60/882,425, filed on Dec. 28, 2006.

(51) Int. Cl.
*A61N 1/00* (2006.01)

(52) U.S. Cl. .......................................................... 607/2

(58) Field of Classification Search ................ 607/2, 27, 607/11, 36, 4, 44, 9, 45; 600/508, 509; 606/1
See application file for complete search history.

(56) References Cited

U.S. PATENT DOCUMENTS

| | | | |
|---|---|---|---|
| 3,837,347 A | 9/1974 | Tower | |
| 3,995,623 A | 12/1976 | Blake et al. | |
| 4,619,246 A | 10/1986 | Molgaard-Nielsen et al. | |
| 4,696,304 A | 9/1987 | Chin | |
| 4,801,297 A | 1/1989 | Mueller | |

(Continued)

FOREIGN PATENT DOCUMENTS

EP 363117 4/1990

(Continued)

OTHER PUBLICATIONS

"EnSite NavX™ Navigation & Visualization Technology." 3 pages, St. Jude Medical. http://www.sjmprofessional.com/Products/US/Mapping-and-Visualization/EnSite-NavX-Navigation-and-Visualization-Technology.aspx Web. Accessed Jun. 19, 2009.

(Continued)

*Primary Examiner* — George Manuel
*Assistant Examiner* — Robert N Wieland
(74) *Attorney, Agent, or Firm* — Harness, Dickey

(57) ABSTRACT

An IMD can be implanted into a patient to address various conditions. The IMD case and leads can have various electrodes and other portions to measure various physiological conditions. For example, a selected current can be generated between two electrodes, either external or internal in the patient, and a voltage can be measured by one or more electrodes of the IMD. A voltage can be measured at two or more locations to determine a relative motion of different electrodes. If the electrodes are in different portions of the heart, a determination can be made of a relative motion or position of the heart or portions of the heart.

45 Claims, 4 Drawing Sheets

U.S. PATENT DOCUMENTS

| | | |
|---|---|---|
| 5,035,246 A | 7/1991 | Heuvelmans et al. |
| 5,078,714 A | 1/1992 | Katims |
| 5,099,845 A | 3/1992 | Besz et al. |
| 5,167,239 A | 12/1992 | Cohen et al. |
| 5,255,680 A | 10/1993 | Darrow et al. |
| 5,265,622 A | 11/1993 | Barbere |
| 5,342,295 A | 8/1994 | Imran |
| 5,385,148 A | 1/1995 | Lesh et al. |
| 5,391,199 A | 2/1995 | Ben-Haim |
| 5,443,489 A | 8/1995 | Ben-Haim |
| 5,480,422 A | 1/1996 | Ben-Haim |
| 5,512,920 A | 4/1996 | Gibson |
| 5,546,951 A | 8/1996 | Ben-Haim |
| 5,558,091 A | 9/1996 | Acker et al. |
| 5,568,809 A | 10/1996 | Ben-haim |
| 5,639,276 A | 6/1997 | Weinstock et al. |
| 5,697,377 A | 12/1997 | Wittkampf |
| 5,713,946 A | 2/1998 | Ben-Haim |
| 5,797,849 A | 8/1998 | Vesely et al. |
| 5,800,407 A | 9/1998 | Eldor et al. |
| 5,840,025 A | 11/1998 | Ben-Haim |
| 5,916,193 A | 6/1999 | Stevens et al. |
| 5,983,126 A * | 11/1999 | Wittkampf .................. 600/509 |
| 6,009,349 A | 12/1999 | Mouchawar et al. |
| 6,088,527 A | 7/2000 | Rybczynski |
| 6,122,552 A | 9/2000 | Tockman et al. |
| 6,152,946 A | 11/2000 | Broome et al. |
| 6,196,230 B1 | 3/2001 | Hall et al. |
| 6,236,886 B1 | 5/2001 | Cherepenin et al. |
| 6,246,468 B1 | 6/2001 | Dimsdale |
| 6,256,121 B1 | 7/2001 | Lizotte et al. |
| 6,301,498 B1 | 10/2001 | Greenberg et al. |
| 6,330,356 B1 | 12/2001 | Sundareswaran et al. |
| 6,389,187 B1 | 5/2002 | Greenaway et al. |
| 6,470,205 B2 | 10/2002 | Bosselmann et al. |
| 6,546,270 B1 | 4/2003 | Goldin et al. |
| 6,569,160 B1 | 5/2003 | Goldin et al. |
| 6,574,498 B1 | 6/2003 | Gilboa |
| 6,595,989 B1 | 7/2003 | Schaer |
| 6,602,271 B2 | 8/2003 | Adams et al. |
| 6,701,176 B1 | 3/2004 | Halperin et al. |
| 6,868,195 B2 | 3/2005 | Fujita et al. |
| 6,888,623 B2 | 5/2005 | Clements |
| 6,892,091 B1 | 5/2005 | Ben-Haim et al. |
| 7,020,522 B1 | 3/2006 | Hoijer et al. |
| 7,047,073 B2 | 5/2006 | Hoijer et al. |
| 7,189,208 B1 | 3/2007 | Beatty et al. |
| 7,207,989 B2 | 4/2007 | Pike, Jr. et al. |
| 7,215,430 B2 | 5/2007 | Kacyra et al. |
| 7,263,397 B2 | 8/2007 | Hauck et al. |
| 7,305,121 B2 | 12/2007 | Kaufmann et al. |
| 7,421,300 B2 | 9/2008 | Smits et al. |
| 7,479,141 B2 | 1/2009 | Kleen et al. |
| 2001/0031920 A1 | 10/2001 | Kaufman et al. |
| 2002/0045810 A1 | 4/2002 | Ben-Haim |
| 2002/0049375 A1 | 4/2002 | Strommer et al. |
| 2002/0111662 A1 | 8/2002 | Iaizzo et al. |
| 2003/0028118 A1 | 2/2003 | Dupree et al. |
| 2003/0055324 A1 | 3/2003 | Wasserman |
| 2003/0078494 A1 | 4/2003 | Panescu et al. |
| 2003/0108853 A1 | 6/2003 | Chosack et al. |
| 2003/0225434 A1 | 12/2003 | Glantz et al. |
| 2004/0001075 A1 | 1/2004 | Balakrishnan et al. |
| 2004/0064159 A1 | 4/2004 | Hoijer et al. |
| 2004/0070582 A1 | 4/2004 | Smith et al. |
| 2004/0097805 A1 | 5/2004 | Verard et al. |
| 2004/0162599 A1 | 8/2004 | Kurth |
| 2004/0215298 A1 | 10/2004 | Richardson et al. |
| 2004/0236395 A1 | 11/2004 | Iaizzo et al. |
| 2004/0249281 A1 | 12/2004 | Olstad |
| 2004/0254437 A1 | 12/2004 | Hauck et al. |
| 2005/0018888 A1 | 1/2005 | Zonneveld |
| 2005/0119550 A1 | 6/2005 | Serra et al. |
| 2005/0187432 A1 | 8/2005 | Hale et al. |
| 2005/0245803 A1 | 11/2005 | Glenn, Jr. et al. |
| 2006/0013523 A1 | 1/2006 | Childers et al. |
| 2006/0058604 A1 | 3/2006 | Avinash et al. |
| 2006/0117773 A1 | 6/2006 | Street et al. |
| 2006/0153468 A1 | 7/2006 | Solf et al. |
| 2006/0173268 A1 | 8/2006 | Mullick et al. |
| 2006/0200049 A1 | 9/2006 | Leo et al. |
| 2006/0206157 A1 | 9/2006 | Hoijer |
| 2006/0229513 A1 | 10/2006 | Wakai |
| 2006/0229594 A1 | 10/2006 | Francischelli et al. |
| 2006/0247520 A1 | 11/2006 | McGee |
| 2007/0016084 A1 | 1/2007 | Denault |
| 2007/0043413 A1 | 2/2007 | Eversull et al. |
| 2007/0046661 A1 | 3/2007 | Ma et al. |
| 2007/0049817 A1 | 3/2007 | Preiss et al. |
| 2007/0123944 A1 | 5/2007 | Zdeblick |
| 2007/0135721 A1 | 6/2007 | Zdeblick |
| 2007/0135803 A1 * | 6/2007 | Belson ............................. 606/1 |
| 2007/0156019 A1 | 7/2007 | Larkin et al. |
| 2007/0164900 A1 | 7/2007 | Schneider et al. |
| 2007/0167801 A1 | 7/2007 | Webler et al. |
| 2007/0252074 A1 | 11/2007 | Ng et al. |
| 2007/0270682 A1 | 11/2007 | Huang et al. |
| 2007/0299351 A1 | 12/2007 | Harlev et al. |
| 2007/0299352 A1 | 12/2007 | Harlev et al. |
| 2007/0299353 A1 | 12/2007 | Harlev et al. |
| 2008/0024493 A1 | 1/2008 | Bordoloi et al. |
| 2008/0038197 A1 | 2/2008 | John et al. |
| 2008/0058656 A1 | 3/2008 | Costello et al. |
| 2008/0071142 A1 | 3/2008 | Gattani et al. |
| 2008/0118117 A1 | 5/2008 | Gauldie et al. |
| 2008/0132800 A1 | 6/2008 | Hettrick et al. |
| 2008/0183072 A1 * | 7/2008 | Robertson et al. ............ 600/425 |
| 2008/0207997 A1 | 8/2008 | Higgins et al. |
| 2008/0243025 A1 | 10/2008 | Holmstrom et al. |
| 2009/0017430 A1 | 1/2009 | Muller-Daniels et al. |
| 2009/0063118 A1 | 3/2009 | Dachille et al. |
| 2009/0103793 A1 | 4/2009 | Borland et al. |
| 2009/0126575 A1 | 5/2009 | Son et al. |
| 2009/0129477 A1 | 5/2009 | Yang |
| 2009/0192381 A1 | 7/2009 | Brockway et al. |
| 2009/0253976 A1 | 10/2009 | Harlev et al. |
| 2009/0262109 A1 | 10/2009 | Markowitz et al. |
| 2009/0262979 A1 | 10/2009 | Markowitz et al. |
| 2009/0262980 A1 | 10/2009 | Markowitz et al. |
| 2009/0262982 A1 | 10/2009 | Markowitz et al. |
| 2009/0262992 A1 | 10/2009 | Markowitz et al. |
| 2009/0264727 A1 | 10/2009 | Markowitz et al. |
| 2009/0264738 A1 | 10/2009 | Markowitz et al. |
| 2009/0264739 A1 | 10/2009 | Markowitz et al. |
| 2009/0264740 A1 | 10/2009 | Markowitz et al. |
| 2009/0264741 A1 | 10/2009 | Markowitz et al. |
| 2009/0264742 A1 | 10/2009 | Markowitz et al. |
| 2009/0264743 A1 | 10/2009 | Markowitz et al. |
| 2009/0264744 A1 | 10/2009 | Markowitz et al. |
| 2009/0264745 A1 | 10/2009 | Markowitz et al. |
| 2009/0264746 A1 | 10/2009 | Markowitz et al. |
| 2009/0264747 A1 | 10/2009 | Markowitz et al. |
| 2009/0264748 A1 | 10/2009 | Markowitz et al. |
| 2009/0264749 A1 | 10/2009 | Markowitz et al. |
| 2009/0264750 A1 | 10/2009 | Markowitz et al. |
| 2009/0264751 A1 | 10/2009 | Markowitz et al. |
| 2009/0264752 A1 | 10/2009 | Markowitz et al. |
| 2009/0264777 A1 | 10/2009 | Markowitz et al. |
| 2009/0264778 A1 | 10/2009 | Markowitz et al. |
| 2009/0265128 A1 | 10/2009 | Markowitz et al. |
| 2009/0267773 A1 | 10/2009 | Markowitz et al. |
| 2009/0297001 A1 | 12/2009 | Markowitz et al. |
| 2010/0030298 A1 * | 2/2010 | Martens et al. ................. 607/45 |
| 2010/0152571 A1 | 6/2010 | Hartmann et al. |

FOREIGN PATENT DOCUMENTS

| | | |
|---|---|---|
| EP | 1393674 A1 | 3/2004 |
| EP | 1421913 A1 | 5/2004 |
| WO | WO-02064040 A2 | 8/2002 |
| WO | WO-2005112836 A2 | 12/2005 |
| WO | WO-2006042039 A2 | 4/2006 |
| WO | WO-2006117773 A1 | 11/2006 |
| WO | WO-2007067945 | 6/2007 |
| WO | WO-2007111542 A1 | 10/2007 |
| WO | WO-2007136451 A2 | 11/2007 |
| WO | WO-2008147961 A1 | 12/2008 |

OTHER PUBLICATIONS

"Local Lisa® Intracardiac Navigation System Model 9670000/9670025." Technical Manual Version 1.2, Chapter 1, pp. 1-19. 2004.

Brenner, David J., Ph.D., "Computed Tomography—An Increasing Source of Radiation Exposure", The New England Journal of Medicine (Nov. 29, 2007), pp. 2277-2284.

Gepstein, Lior, M.D., "A Novel Method for Nonfluoroscopic Catheter-Based Electroanatomical Mapping of the Heart, In Vitro and In Vivo Accuracy Results", American Heart Association, Learn and Live, Circulation (1997), http://circ.ahajournals.org/cgi/content/abstract/95/6/1611 printed Oct. 2, 2008.

International Preliminary Report on Patentability and Written Opinion for PCT/US2009/040998 mailed Oct. 28, 2010, 2009 claiming benefit of U.S. Appl. No. 12/421,332, filed Apr. 9, 2009; which claims priority to U.S. Appl. No. 61/105,957, filed Oct. 16, 2008; U.S. Appl. No. 12/117,549, filed May 8, 2008.

International Preliminary Report on Patentability and Written Opinion for PCT/US2009/0400984 mailed Oct. 28, 2010, claiming benefit of U.S. Appl. No. 12/117,549, filed May 8, 2008.

International Preliminary Report on Patentability and Written Opinion for PCT/US2009/040979 mailed Oct. 28, 2010 claiming benefit of U.S. Appl. No. 12/117,537, filed May 8, 2008.

International Search Report and Written Opinion for PCT/US2008/088189 mailed Apr. 3, 2009, claiming benefit of U.S. Appl. No. 12/183,796, filed Jul. 31, 2008; and claims priority to U.S. Appl. No. 11/966,382, filed Dec. 28, 2007.

International Search Report and Written Opinion for PCT/US2009/0400984 mailed Sep. 21, 2009, claiming benefit of U.S. Appl. No. 12/117,549, filed May 8, 2008.

International Search Report and Written Opinion for PCT/US2009/040998 mailed Jul. 29, 2009 claiming benefit of U.S. Appl. No. 12/421,332, filed Apr. 9, 2009; which claims priority to U.S. Appl. No. 61/105,957, filed Oct. 16, 2008; U.S. Appl. No. 12/117,549, filed May 8, 2008.

International Search Report and Written Opinion for PCT/US2009/067486 mailed May 4, 2010, claiming benefit of U.S. Appl. No. 12/336,085, filed Dec. 16, 2008.

International Search Report and Written Opinon for PCT/US2009/040979 mailed Sep. 21, 2009 claiming benefit of U.S. Appl. No. 12/117,537, filed May 8, 2008.

Invitation to Pay Additional Fees for PCT/US2009/0400984 mailed Jul. 30, 2009, claiming benefit of U.S. Appl. No. 12/117,549, filed May 8, 2008.

Invitation to Pay Additional Fees for PCT/US2009/040979 mailed Jul. 30, 2009 claiming benefit of U.S. Appl. No. 12/117,537, filed May 8, 2008.

Invitation to Pay Additional Fees for PCT/US2009/067486 mailed Mar. 5, 2010, claiming benefit of U.S. Appl. No. 12/336,085, filed Dec. 16, 2008.

Invitation to Pay Additional Fees mailed Jul. 7, 2010 for PCT/US2010/030534 claiming benefit of U.S. Appl. No. 12/421,375, filed Apr. 9, 2009.

Jiang, Yuan. "An Impedance-Based Catheter Poisitioning System for Cardiac Mapping and Navigation." IEEE Transactions on Biomedical Engineering, (Aug. 2009) pp. 1963-1970, vol. 56, No. 8.

Markowitz, Toby, et al., "Unleaded: The Fluoroless 3D Lead Implant", Presented at Heart Rhythm Society, Denver, CO, (May 2007) 1 pg.

Markowitz, Toby, et al., Abstract Submission, "Unleaded: The Fluoroless 3D Lead Implant", Mar. 2007 2 pgs.

Milstein, S. et al., "Initial Clinical Results of Non-Fluoroscopic Pacemaker Lead Implantation." (pre-presentation abstract) May 14-17, 2008. 2 pgs.

Milstein, S. et al., "Initial Clinical Results of Non-Fluoroscopic Pacemaker Lead Implantation." (poster presentation) May 14-17, 2008. 1 pg.

Nelder, J.A., et al. "A simplex method for function minimization." vol. 7, Issue 4, (1965) pp. 308-313.The Computer Journal.

Savage, George, M.D., "Electric Tomography (ET)—A Novel Method for Assessing Myocardial Motion and Cardiac Performance", Heart Rhythm Society, Denver, CO (May 9-12, 2007) 1 pg.

Wittkampf, Fred, H.M., et al., "LocaLisa: New Technique for Real-Time 3-Dimensional Localization of Regular Intracardiac Electrodes." Circulation Journal of the American Heart Association, 1999; 99; 13-12-1317.

Wittkampf, Fred., H.M., et al. "Accuracy of the LocaLisa System in Catheter Ablation Procedures." Journal of Electrocardiology vol. 32 Supplement (1999). Heart Lung Institute, University Hospital Utrecht, The Netherlands.

Invitation to Pay Additional Fees for PCT/US2010/047241 mailed Jan. 10, 2011, claiming benefit of U.S. Appl. No. 12/844,065, filed Jul. 27, 2010.

* cited by examiner

SYSTEM AND METHOD TO EVALUATE ELECTRODE POSITION AND SPACING

CROSS-REFERENCE TO RELATED APPLICATIONS

This application is a continuation-in-part of U.S. patent application Ser. No. 11/966,382 filed on Dec. 28, 2007, which application claims the benefit of U.S. Provisional Application No. 60/912,610, filed on Apr. 18, 2007; U.S. Provisional Application No. 60/882,420, filed on Dec. 28, 2006; U.S. Provisional Application No. 60/882,431, filed on Dec. 28, 2006; U.S. Provisional Application No. 60/882,435, filed on Dec. 28, 2006; U.S. Provisional Application No. 60/882,428, filed on Dec. 28, 2006; U.S. Provisional Application No. 60/882,430, filed on Dec. 28, 2006; and U.S. Provisional Application No. 60/882,425, filed on Dec. 28, 2006. The entire disclosures of the above applications are incorporated herein by reference.

FIELD

The present disclosure generally relates to implantable medical devices, and particularly relates to measuring anatomical features and determining effectiveness of selected treatments.

BACKGROUND

The statements in this section merely provide background information related to the present disclosure and may not constitute prior art.

Implantable medical devices (IMD) can be provided for various purposes. For example, IMD's can be provided for pacing or providing other cardiac therapies to a heart of a patient. The pacing can assist in treating arrhythmias or other diagnosed conditions in a patient.

IMD's are generally permanently implanted into a patient. The IMD includes one or more electrodes that are in contact with a portion of the patient. For example, an electrode can be implanted in a right atrium (RA), a right ventricle (RV), and a left ventricle (LV). The various leads can include one or more electrodes that can deliver a current, sense/measure a voltage, measure an impedance, or other appropriate configurations. In addition, the IMD can include a main body that can also include or form an electrode.

SUMMARY

An IMD can be implanted into a patient to address various conditions. The IMD case and leads can have various electrodes and other portions to measure various physiological conditions. For example, a selected current can be delivered between two electrodes, either external or internal in the patient, and a voltage can be measured by one or more electrodes of the IMD. A voltage can be measured at two or more locations to determine a relative motion of different electrodes. If the electrodes are in different portions of the heart, a determination can be made of a relative motion or position of the heart or portions of the heart.

Further areas of applicability will become apparent from the description provided herein. It should be understood that the description and specific examples are intended for purposes of illustration only and are not intended to limit the scope of the present disclosure.

DRAWINGS

The drawings described herein are for illustration purposes only and are not intended to limit the scope of the present disclosure in any way.

DETAILED DESCRIPTION

The following description is merely exemplary in nature and is not intended to limit the present disclosure, application, or uses. While the subject disclosure includes a detailed description of an implantable medical device for pacing, it is readily appreciated these and similar devices may be applied to an Implantable Cardioverter Defibrillator (ICD).

Figure 1:
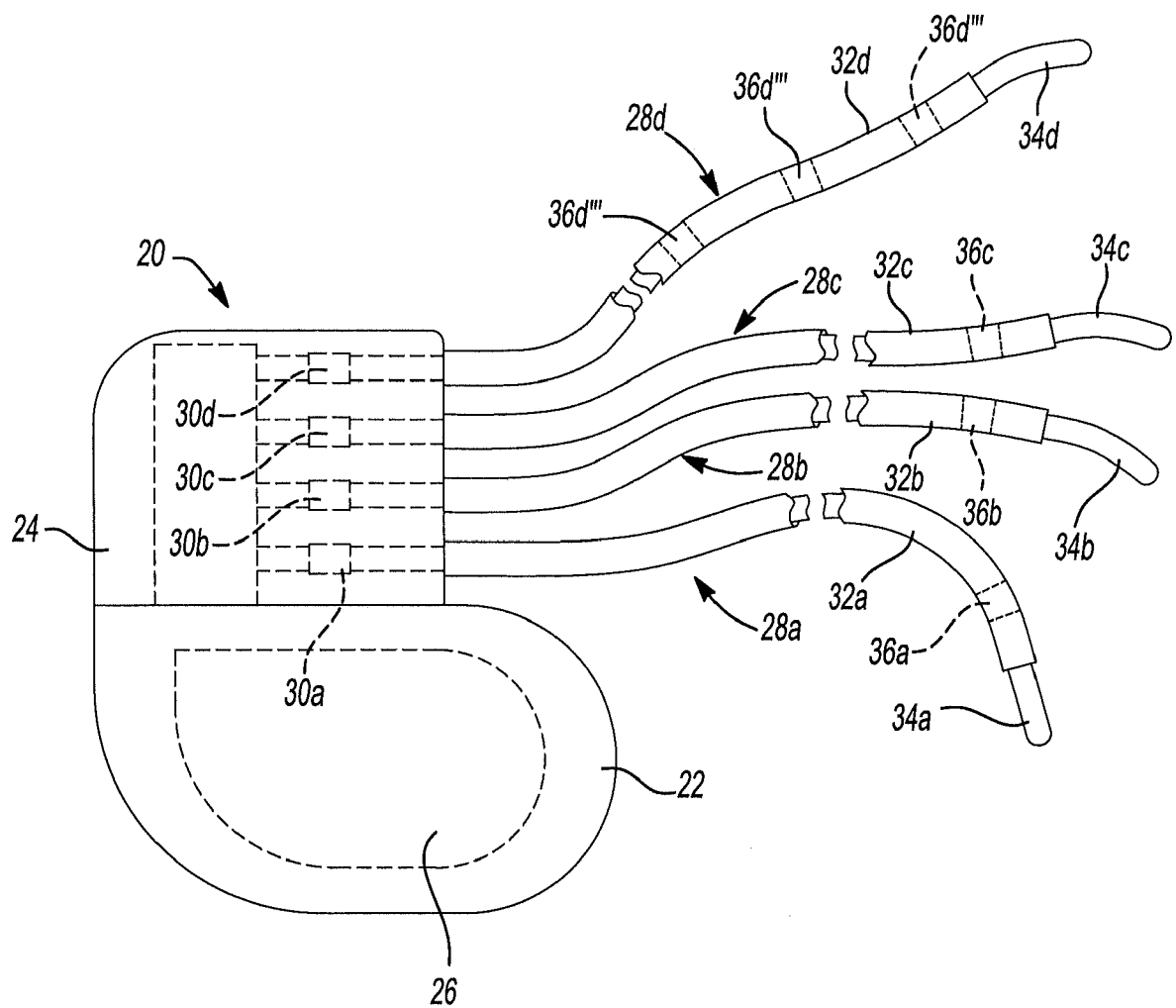
FIG. 1 is a plan view of an IMD, according to various embodiments.
Figure 2:
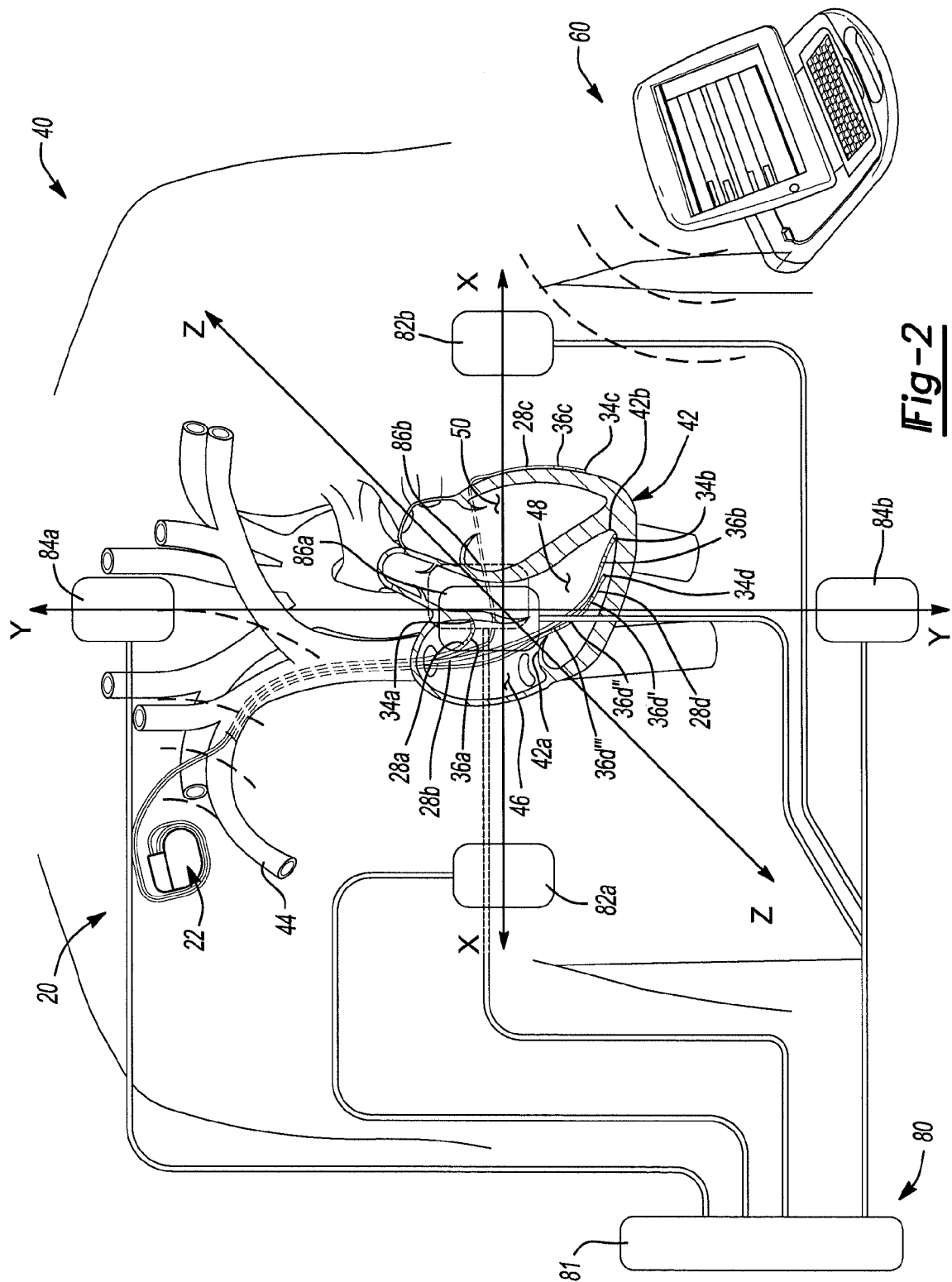
FIG. 2 is an environmental view of a patient, an IMD, an external programmer, and a bioimpedance system, according to various embodiments.

With reference to FIGS. 1 and 2, an implantable medical device (IMD) 20 is illustrated. It will be understood that the IMD 20 can include the specific portions disclosed herein, such as a tri-lead or quad-lead medical device, or can include any other appropriate portions. The IMD 20 can include any appropriate number of leads and electrodes. The IMD 20, however, generally includes a body or case portion 22 and a lead connector block 24. Positioned within the case 22 can be one or more, processors, electronic circuits, batteries, or the like in a circuitry or internal electronics system 26. The internal electronics system 26 is discussed further herein in greater detail. The electronics system 26 can be used to generate pacing signals or process signals sensed from the leads.

Interconnected with the lead connector block 24 can be a first lead 28a, a second lead 28b, a third lead 28c and a fourth lead 28d. Each of the leads 28a-28d can include respective lead block connection portions 30a-30d. Each of the leads can also include a respective sheath or insulation portion 32a-32d and respective lead tips or tip electrodes 34a-34d. It will be understood that each of the leads 28a-28d can also include multiple electrodes, such as optional ring electrodes 36a-36d. Accordingly, it will be understood that each of the leads 28a-28d can include one or more electrodes, for various purposes, such as sensing, defibrillation, pacing, or other appropriate purposes. Various leads such as the lead 28d, can also include multiple ring electrodes 36d'-36d''' for use in gathering information regarding the heart, as further discussed herein.

The IMD 20 can be positioned within a patient 40 as illustrated in FIG. 2. The IMD 20 can be positioned in any appropriate portion of the anatomy of the patient 40, such as generally in a thoracic cavity, a shoulder area, or other appropriate portion of the patient 40. The leads 28a-28d can be positioned within a heart 42 of the patient 40 in any appropriate manner, such as by guiding the leads 28a-28d through the superior vena cava 44. The leads 28a-28d can be attached or fixed to a wall of the heart 42. For example, tip electrodes 34a-34d can include a helix that is screwed into a wall of the heart 42. It will be understood, that the leads 28a-28d or any appropriate lead can be implanted in any appropriate portion of the patient 40, such as in or near the liver, spleen, diaphragm, etc.

The leads can be positioned in any appropriate portion of the anatomy, such as positioning the first lead 28a in a right atrium 46, positioning the second lead 28b in the right ventricle 48, and positioning the third lead 28c in the left ventricle 50. It will be understood that the leads can be implanted at any appropriate location within the heart 42, such as near the tricuspid valve 42a, near a ventricle apex 42b, or any other appropriate specific location. The electrodes 36d'-36d''' of the lead 28d can be provided solely for gathering and sensing position information. Accordingly, those may be located against a wall of the heart 42. Pacing and defibrillation leads 28a-28c can be positioned generally within at least three regions of the heart 42 for pacing the heart 42, for providing defibrillation into the heart 42, or other appropriate purposes.

An external programmer 60 can be provided to transmit information to, receive information from, and program the IMD 20. The information can be transmitted, or communicated via a wire or substantially wirelessly using telemetry circuitry in the internal electronics system 26, as discussed further herein. The IMD 20 can also sense and store information and transmit it to the external programmer 60 and also receive information or instructions, such as programming, from the external programmer 60, further discussed herein. A processor within the IMD 20 can also be used to alter a therapy based upon sensed information.

According to various embodiments, with reference to FIG. 2, the IMD 20 can be implanted in the patient 40. Selected information can be acquired regarding the heart 42, such as collecting chronic measurements for follow-up of the patient 40. The information can also include position information of the various electrodes. The position information can be used to determine various measurements relating to the heart 42. For example, volume changes and dimension changes can be determined. A bioimpedance system 80 can be used to cooperate with the IMD electrodes to acquire this information.

Current can be passed through the patient with the bioimpedance system 80. The bioimpedance system 80 can include a controller and a generating module 81 that drives three pairs of patch electrodes. The patch electrodes can be provided in pairs to form three orthogonal axes, such as an X-axis, a Y-axis and a Z-axis. For example, a first pair of patch electrodes 82a, 82b can inject a current through the patient 40 to form the X-axis. A second pair of patch electrodes 84a and 84b can be positioned on the patient 40 to inject a current form a Y-axis. Finally, two patch electrodes 86a and 86b can be positioned on the patient 40 to inject a current along the Z-axis.

The patch electrodes 82a-86b can be used to inject a current through the patient 40 in any appropriate manner. For example, the patch electrodes used to inject a current can be similar to those disclosed in U.S. Pat. No. 5,697,377, issued on Dec. 16, 1997. Another appropriate system for injecting current is similar to the Localisa™ intracardiac navigation system, sold by Medtronic, Inc. having a place of business in Minneapolis, Minn. It will be understood that the bioimpedance system (EP system) 80 can include various portions that are different from the specifics discussed above, but can generally inject a current within the patient 40 in a similar manner.

Generally, a current of a selected frequency is delivered within the patient 40 through patches 82a-86b. As the current passes through the tissue, a voltage drop occurs as a result of the impedance of the tissue. This voltage can be measured along the corresponding X, Y, and Z axes. For example, muscle tissue, fluid filled organs (such as blood vessels or veins or the heart) are sufficiently conductive to allow for a voltage drop across different areas that can be measured with the electrodes of the leads 28a-28d or even the electrode of the case 22. These voltages can be related to the position of the electrodes based upon knowing the delivered currents. In addition, relative positions of the electrodes can be determined based upon a change in sensed voltage over time.

The patch electrodes 82a-86b can be positioned on the patient 40 using any appropriate mechanism, such as appropriate or tolerated adhesives, or other appropriate means. The patches are generally placed in conductive contact with the skin of the patient 40 to allow for delivery of the current through the internal organs and tissue of the patient 40. The current can generally be about 0.01 mA to about 2.00 mA, including about 1.0 mA. The current is generally injected as an alternating current at about 30 kHz, including about 5 kHz to about 50 kHz.

As discussed above, the IMD 20 and the respective leads 28a-28d are generally positioned within the patient 40. The injection of the current between the patches 82a-86b can generate a voltage that can be measured by the electrodes 34a-36c of the IMD 20 without further invasive procedures. That is, the IMD 20 and leads 28a-28d are already within the patient 40 and no additional internal electrodes are necessary to be introduced into the patient such as by the use of a catheter, etc. As discussed further herein, the measurements of the voltage(s) within the patient 40 can be used to determine positions of the various electrodes that are within the patient 40. The determined position of the electrodes can be used to determine conditions and measurements of the patient 40, such as cardiac dimensions or positions.

Figure 3:
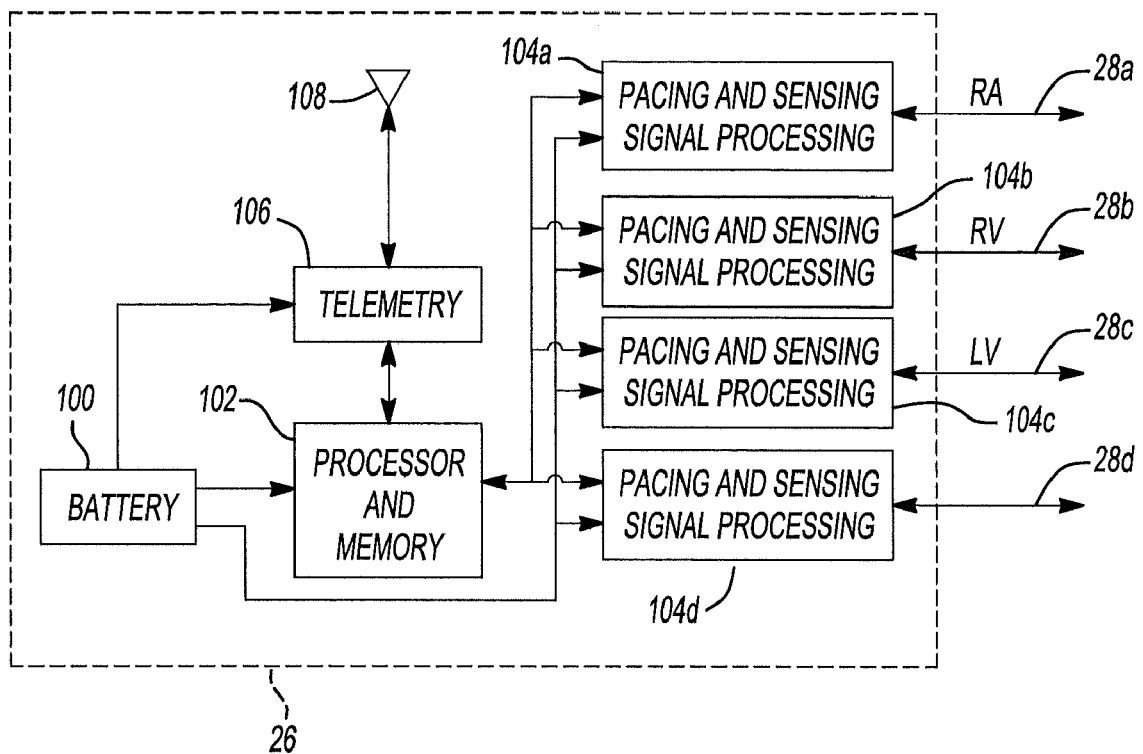
FIG. 3 is a block diagram of an electronic system of an IMD, according to various embodiments.

With reference to FIG. 3, the electronics system 26 of the IMD 20 is illustrated. The electronics system 26 can be positioned within the IMD 20 in any appropriate manner and is diagrammatically illustrated. The electronics system 26 of the IMD 20, can include a battery or other power storage device 100 to power the electronics system 26. The battery 100 can transmit power to a processor and memory (P&M) module 102 of the electronics system 26. The processor can be any appropriate processor, such as a processor operable to process signals received from the leads 28a-28d and send instructions, such as signals, to the leads 28a-28d. In addition, the P&M module 102 can include a memory module, either integrated with or in communication with the processor, to store sensed signals from the leads 28a-28d, processed data and programming information from the external programmer 60, discussed above.

The P&M module 102 can be interconnected or in communication with a pacing and sensing signal processing (PSS) module 104. It will be understood that more than one PSS module 104, such as PSS modules 104a-104d, can be provided with the IMD 20, such as a distinct PSS module for each of the leads 28a-28d. Each PSS module 104 can receive and send information to and from the P&M module 102 as well as from leads 28a-28d. Further, each of the PSS modules can include the modules and/or circuitry discussed further herein relative to the exemplary PSS module 104. The information from P&M module 102 can direct the PSS module 104 to output a pacing stimulus to a connected lead, 28a-28d. The occurrence of sensing can be communicated to P&M module 102 from PSS module 104. The battery can power the PSS module 104. The PSS module 104 is in communication with the leads 28a-28d that are attached to various portions of the patient 40.

The P&M module 102 can also be in communication with a telemetry module 106 connected to an antenna 108. The telemetry module 106 and the antenna 108 can also receive power from the battery 100, either directly or through the P&M module 102. The telemetry module 106 and the antenna 108 can send and receive information that is processed by the processor or stored in the memory of the P&M module 102. The transmission can be to and from an external source, such as the external programmer 60 or the external bioimpedance system 80. As discussed further herein, the telemetry module 106 can send stored sensed information, processed or stored position information, or other appropriate information.

The P&M module 102 can control timing, detection, sensing, pacing, telemetry, and other functions. Generally, the P&M module 102 can perform functions necessary for pacing functions, diagnostic functions and for follow-up information that is telemetrically transmitted. As is understood, the IMD 20 can be provided for pacing of the heart 42 of the patient 40 in any appropriate and programmed manner. The P&M module 102 can send a signal to the PSS module 104, which can, in turn, send a pacing signal through each of the leads 28a-28c and sense signals from each of the leads 28a-28d.

Figure 4:
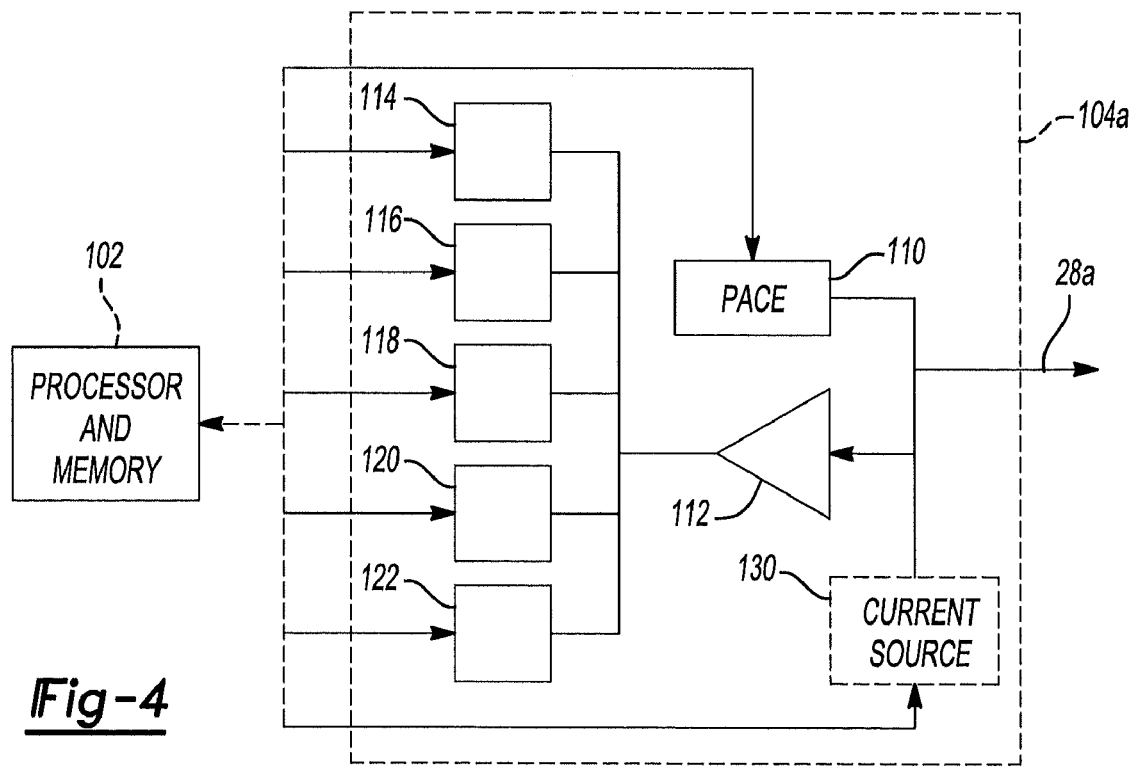
FIG. 4 is a detail block diagram of a portion of an electronic system of an IMD, according to various embodiments.

With additional reference to FIG. 4 and continuing reference to FIG. 3, a detailed view of the PSS module 104 is illustrated. Each of the leads, such as the lead 28a, communicates with the PSS module 104. Each of the leads can be connected to a separate PSS module 104, or a multiplex switch, as discussed herein can be used to allow communication between each of the leads 28a-28d and the single PSS module 104. The PSS module 104 can include various distinct and selected portions, such as those illustrated in FIG. 4. The various components discussed in detail here are exemplary and can be selected according to various embodiments.

Initially, as discussed above, each of the leads can be in communication with a pace module such as module 110. The pace module 110 can combine and transmit a selected pacing stimulus pulse as well as current, of select frequencies to the electrode 28a, based upon instructions or commands from the P&M module 102 and power from the battery 100. Providing a pacing stimulus pulse through the lead 28a is generally known and will not be discussed in detail here.

A sensed signal can also be received through amplifier module 112 to deliver an amplified sensed signal to one or all of the filter or function modules including electrograms 114, myocardial infarction detection 116, sensing for timing and rhythm detection 118, evoked response 120, or impedance/position signal detection 122.

In the electrogram module 114, signals can be processed and sent to the P&M module 102 for telemetry to the external programmer 60. The electrogram signal can also be communicated to the P&M module 102 for analysis and interpretation by the P&M module 102 thus, altering treatment based upon the electrogram module 114.

The pacing and sensing signal processing module exemplified by module 104 can include signal filters for processing information in various spectral portions to isolate electrograms, the electrical signal from electrodes in or on the heart that reflect electrical activation, for example, from lead 28a. The electrogram information can be sent through the telemetry module 106 and antenna 108 to the external programmer 60 for display and/or assisting in augmenting or programming the IMD 20. The electrogram signals can be used to assist in programming the IMD 20.

The electrogram circuitry within module 114 can include various band pass filters to assist in receiving an appropriate signal for processing and/or transmission to the external programmer 60. For example, a band pass of about 1 to 500 Hz can be provided.

The system for analysis of cardiac repolarization, ST segment analysis, such as might be used to detect a myocardial infarct, could utilize circuitry within module 116. A band pass filter of about 0.1 to about 40 Hz can be used to allow for the low frequency constituents necessary for the ST segment to be detected.

Detection of ventricular or atrial depolarizations for timing purposes within the IMD 20 can be accomplished utilizing circuitry within module 118. Such circuitry may contain a bandpass filter of 1 to 30 Hz to detect cardiac activity while avoiding detection of signals due to activation of skeletal muscle, radiation from devices operated by main power at 50 or 60 Hz or recharging of the pacing stimulus output capacitor.

Evoked response detection enabling the IMD 20 to detect whether a pacing stimulus met conditions to capture the heart may be accomplished by circuitry within module 120.

Detection of electrode movement can be accomplished by circuitry within module 122. By injecting a current through lead 28a, from current source 130, an electric field can be established within cardiac tissue or other tissue of interest. Detection and analysis of the resultant sensed voltage due to the injected current can be used to measure and establish movement of cardiac tissue. Analyzing the signals that relate to the frequency of the injected current allows for the determination of the heart's motion 42. If, for example, the injected current is about 30 kHz, then a band pass range of about 25 to about 35 kHz in circuit module 122 could be used to assist in detecting a signal from the lead 28a and determining motion. Analysis of the signal to determine motion can be used by a P&M module 102 to both provide for cardiac pacing and/or defibrillation of the heart for the patient 40. Motion may be used to determine whether an alteration in pacing or defibrillation is required.

The relatively high frequencies used for measuring impedance in the patient 40 can result in relatively high current drain in the IMD 20. Sampling of signals in order to provide a faithful reproduction from current injected in the range of 30 kHz may require sampling intervals such that the sampling frequency is above the Nyquist criteria of twice the fundamental frequency of 30 kHz. That is, sampling of 60 kHz would be required to provide a faithful reproduction. For a long term implantable device, this represents considerable sampling and, therefore, current drain from the battery 100. A technique of undersampling can be used with intentional aliasing of the impedance signal. By undersampling, the signal can be produced that includes substantially the desired and necessary information for transmission, but at a lower current drain.

Each of the processed signals as mentioned above can be telemetrically sent to an external component, such as a bioimpedance system 80 or external programmer 60 by way of the telemetry 106 and antenna 108. In addition, each signal can be used for various purposes, such as a determination of a position of the electrodes, programming or sending information regarding the IMD 20, or of the patient 40. The signals can also be used internally in the IMD 20 to alter the pacing signal by the P&M module 102. It will be further understood that the filters mentioned above can be of any appropriate design, such as an analog or digital design.

With further reference to FIG. 4, a current source module 130 can be optionally provided as a part of the PSS module 104. The current source module 130 can be used to direct a current through any appropriate electrodes of the IMD 20, including those of the leads 28a-28d or the case 22. The current source 130 can deliver a current through the patient 40 when the external bioimpedance system 80 is not present.

Electrodes of leads 28a-28d can be used to measure voltage changes over time to determine relative motion of selected portions of the heart 42, or any appropriate portion. For example, a voltage can be measured in the right ventricle for determination of right ventricular stroke volume or other measurements over time by sensing the voltage over time.

Once the IMD 20 including the various electrodes 28a-28d, or any appropriate number of leads is implanted in the patient 40, selected electrodes can be used to determine positions of other selected electrodes. For example, the patch electrodes 82a-86b can be used to inject current that can be sensed with the electrodes of the IMD 20. According to various embodiments, two of the electrodes of the IMD 20 can also or alternatively be used to inject a current from the current source 130 into the patient 40 to generate a voltage to be sensed by another of the electrodes of the IMD 20. For example, the distal electrode 34b of the lead 28b can be a first electrode and the case 22 can be a second electrode.

The case electrode 22 and the distal tip electrode 34b can be used to inject a current through the tissue of the patient 40. Any of the electrodes between the case electrode 22 and the distal tip electrode 34b can be used to measure a voltage. Accordingly, a current injected from the current source 130 and transmitted through the case electrode 22 and the distal tip electrode 34b and can be used to generate a voltage at any of the electrodes between the case electrode 22 and the distal tip electrode 34b. These voltages can be measured and transmitted through the position sensing module 122 for processing by the P&M module 102 and transmission with the telemetry module 106 or for saving in the P&M module 102.

By injecting the current with an implanted electrode within the patient 40, error produced by positioning an electrode patch, such that the patches 82a-86b, on a surface of the patient's 40 skin can be reduced or eliminated. In addition, by using the electrodes implanted as a part of the IMD 20, the IMD 20 can provide a current injection at any time without the need of external or additionally applied current patches of the bioimpedance system 80. For example, the IMD 20 can be programmed to determine a location of a selected electrode 5 times over a selected period. The IMD 20 can, therefore, provide the injected current and measure a voltage at the selected electrode without additional instruments. Accordingly, the electrodes of the IMD 20 can be used to provide substantially efficient measurements of the positions of electrodes implanted as a part of the IMD 20, which correlate to various anatomical features or conditions. As discussed here, the positions of the electrodes of the leads 28a-28d can be measured to determine stroke volume, ejection fraction, dimensions of selected chambers of the heart, and various other hemodynamic indices for the RV, LV, and a combination of RV and LV dimensions. In addition, when electrodes are positioned in appropriate locations, such as on opposite sides of a heart wall, a heart wall thickness or change in thickness can also be measured.

The positions of the electrodes are determined based upon the measured voltages, such as in the Localisa™ intracardiac navigation system sold by Medtronic, Inc. The electrodes of the IMD 20, however, are not directly connected to the external bioimpedance system 80. Because the leads and electrodes positioned within the patient 40 are not directly connected to the bioimpedance system 80, a determination of which axis, X, Y, or Z, current is being injected must be provided. According to various embodiments, a time division multiplex system can be provided to allow for injection of each of the different axes at a substantially different time.

Figure 5:
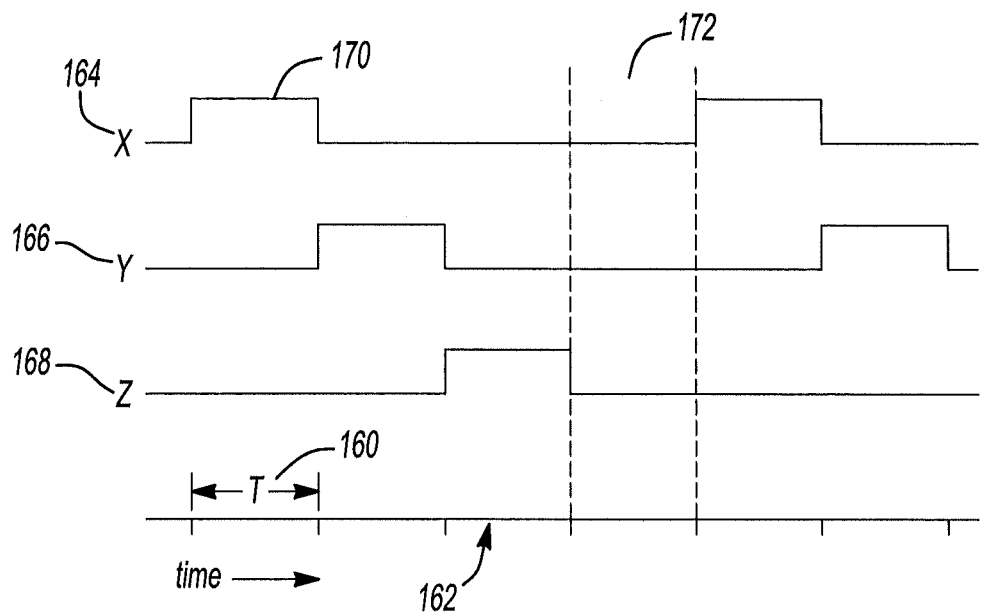
FIG. 5 is a graphical illustration of a sequenced signal.

In a time division multiplex system, a current at each of the axes can be injected at a different time within the patient 40 as illustrated in FIG. 5. As illustrated in FIG. 2, the patches 82a-86b can be positioned on the patient 40. During a first time, the patches 82a and 82b can be energized to inject a current within the patient 40. At a second time, the patches 84a and 84b can be energized, and at a third time, the patches 86a and 86b can be powered to deliver the current along the respective axes.

According to one example, the generator 81 is operable to inject a current at an appropriate frequency into the patient 40 through the patch electrodes 82a-86b. The wave of the generator 81 can include any appropriate frequency and can be selected for various purposes, such as a sampling rate, a power drain, and other appropriate purposes. The generator 81 can also include a switch to allow for switching between selected pairs of the patch electrodes 82a-86b over any period of time, including any appropriate number of cycles.

According to various embodiments, the generator 81 can generate a frequency of about 30 kHz and can switch between each of the patch electrode pairs at any appropriate time interval, such as interval T 160, illustrated in FIG. 5. As illustrated in FIG. 5, time is illustrated on an x-axis 162. Substantially parallel to the time axis 162 are lines illustrating the X-axis patch electrodes 164, the Y-axis patch electrodes 166, and the Z-axis patch electrodes 168. An active current pulse 170 illustrates that current is directed to the respective patches at a sequential time period T. In addition, a rest or null period 172 is provided between each series of injecting current along the X, Y and Z axes through the patch electrodes 82a-86b.

If the frequency of the generator 81 is selected to be 30 kHz and a sample is selected to be measured with an electrode of the IMD 20 every ten cycles, then a sample would be taken approximately every 330 microseconds during each activated period 170. Because there are four distinct time periods T, each activation of the axes and the null 172, time period T occurs every approximately 1.3 milliseconds, which allows about 770 samples per second. Although this would provide a large amount of data relating to the position of the various electrodes, this could also create a large drain on the battery 100 of the IMD 20 and require a large amount of data transmission.

Accordingly, it can be selected to reduce the frequency of the generator 81 and further increase the length of time interval T 160 to reduce the amount of data transmission or battery drain and increase signal to noise ratio in the position detection circuitry 122 of the IMD 20. For example, the frequency of the generator 81 could be about 3 kHz. To allow 100 cycles of the 3 kHz signal requires time period T to be about 33 milliseconds in length, allowing for about 7.5 samples per second. This sampling frequency can be selected to achieve a selected collection of information regarding the heart 42.

Nevertheless, it will be understood that any appropriate frequency can be selected to achieve an appropriate sampling rate of the heart 42 for the position sensing module 122. For example, it can be selected to provide a sample frequency of about ten to fifty samples per second, including about twenty to about sixty samples per second. It will be understood that the sample frequency can be created depending upon a time period T and frequency of the generator 81. For example, a frequency of the generator of about 10 kHz and a time period T of about fifty cycles could greatly increase the sampling frequency of the position sensing module 122.

As discussed above, the position information can be used to determine various characteristics of the heart 42. For example, a high data sample rate can be used to identify substantially accurate and detailed mechanical features of the heart 42. In addition, various disease conditions can be determined, measured based upon the determined positions of the electrodes of the IMD 20, or used in combination with other sensors to detect or assist in detection or fibrillation, chamber volume, and other appropriate details.

In addition, the sequencing as illustrated in FIG. 6, allows for synchronization between the generator 81 and the position sensing module 122. For example, the position sensing module 122 can be programmed or hard-wired regarding the sequence of the powering of the axes of the patch electrodes 82a-86b. That is, the position sensing module 122 can know that the patches sequentially energize the X, Y, and Z axes. The null period 172 can be easily detected as a starting point so that the position sensing module 122 can determine the sequencing of the axes energizing. That is, after the null period 172, the next signal sensed is known to be the X-axis. Accordingly, the null time 172 can be an efficient and low power mechanism to synchronize the position sensing module 122 and the generator 81.

Additional synchronization methods include providing a timing device in both the IMD 20 and the external bioimpedance system 80. The timing devices in the IMD 20 and in the external bioimpedance system 80 can be synchronized at a selected time, such as prior to implantation or with a synchronizing signal. At any time thereafter, the two timing devices are substantially synchronized. Accordingly, when the bioimpedance system 80 powers a selected set of patches, a time signal or determination can also be made. When the impedance is measured by the electrodes of the IMD 20, a time stamp can also be generated. Accordingly, when the measurements are telemetrically sent, the time stamp of the IMD 20 is also sent with the measurements and can be correlated to the time of the injection of the selected axis.

A third synchronization method can use the telemetric system 106 of the IMD 20. A telemetric system 106 can also be provided with the bioimpedance system 80 so that a signal can be sent to the IMD 20 that a selected axis is being powered. Accordingly, the sensed or measured voltage can then be associated with a selected axis of the bioimpedance system 80. This can allow the electrodes associated with the IMD 20 to relate the sensed voltage with an appropriate axis of the bioimpedance system 80.

Other synchronization systems can also be provided. For example, a frequency multiplex system can be used to distinguish the axes of the bioimpedance system 80. For example, each of the three axes, X, Y and Z, can be injected at substantially different frequencies. For example, a current signal along the X axis can be generated at about 31 kHz, the Y axis can be generated at about 32 kHz, and the Z axis can be generated at about 33 kHz. Selected filters can be provided in the position sensing module 122 to distinguish the three frequencies. The band pass filters can allow the selected frequency signal to pass to the P&M module 102.

Sensing a voltage, transmitting the sensed voltage or position information, or other information can cause a power drain from the battery 100. The IMD 20, including the battery 100, is implanted in the patient 40 for a selected period of time. At a particular current drain on the battery 100 a certain service life of the IMD 20 will occur. An average drain can be calculated based on a duty cycle utilization of a system, such as a position sensing module 122. Accordingly, sampling of the voltage detection can be at a selected rate and transmitted with the telemetry system 106 to assure no more than a selected current drain will occur.

As discussed above, it can be selected to demodulate the detected signals from the generated axes to provide a lower frequency signal for transmission from the IMD 20. As discussed above, the injected current generated can be at about 30 kHz. Nevertheless, the demodulation and filtering can provide a signal that is about 100 Hz, such as about 10 to about 500 Hz.

Figure 6A:
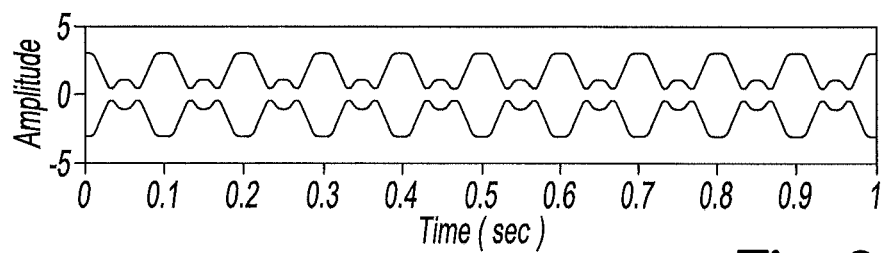
FIGS. 6A-6C illustrate graphical illustrations of wave forms and undersamplings of signals.

As an example, the frequency of the injected current may be about 10 kHz. For example, the three axes X, Y and Z can each be injected into the patient 40 at a different frequency such as 10.01 kHz, 10.02 kHz, and 10.03 kHz. With reference to FIG. 6A, three sinusoid waves at 10.01, 10.02, and 10.03 kHz are illustrated. FIG. 6A shows the envelope of the overlapping waves. As discussed above, transmission of data from such high frequencies, such as with the electrodes that are sensing a voltage, would require high bandwidth and a corresponding high drain on the battery 100.

Figure 6B:
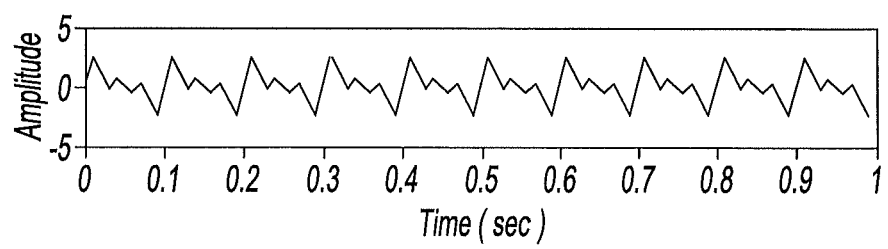

In an attempt to reduce the bandwidth required to transmit the signal of the sensed voltage, the signal can be undersampled at, for example, 100 Hz. As illustrated in FIG. 6B, an undersampled signal is far less dense than the complete signal illustrated in FIG. 6A. Due to aliasing, however, the original signal can not be fully recovered to determine the voltage sensed with the electrodes of the leads 28a-28d to allow for the determination of a position of the electrodes, as discussed above.

Figure 6C:
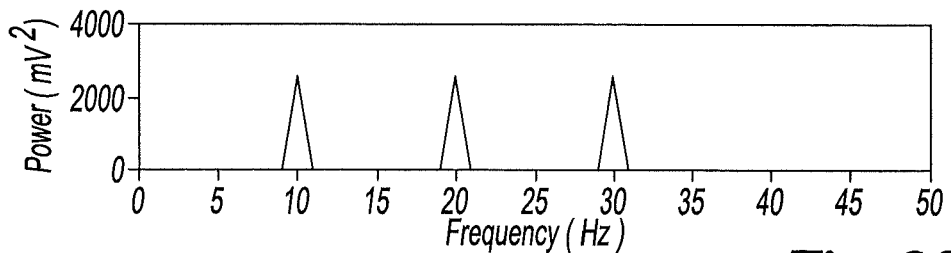

If a transformation, such as a fast Fourier transformation, is performed on the undersampled signal in the frequency domain, the three signal components, those at 10, 20 and 30 Hz above the base line 10 kHz, can be observed, as illustrated in FIG. 6C. The transformation allows the amplitude portion of the signal to be measured at the various frequencies above the baseline. If the signals are measured over time, such as at a selected sampling rate, information regarding the position of the electrodes can be determined.

The transformation can be performed by executing instructions with a selected processor. The processor can be positioned in the external bioimpedance system 80, the external programmer 60, or even as a part of the processor 102. It will be understood that a processor can execute instructions to determine a Fourier transformation of the undersampled signal in the frequency domain to detect the three signal components, or any appropriate number of signal components. It will be understood that the transformation can occur either before or after telemetry of information from the IMD 20, for selected purposes, such as reducing a processing load on the IMD 20 or for other appropriate reasons. In addition, as discussed above, the IMD 20 including the P&M module 102 can alter various programming of the IMD 20, such as a pacing program based upon the determined positions. Accordingly, providing processing of the Fourier transformation in the P&M module 102 can assist in determining position information of the various electrodes associated with the IMD 20.

The sensed voltage can be used to determine positions of the various electrodes of the leads 28a-28d. The voltages can be sensed substantially continuously when a current is injected. The positions of the electrodes can be determined using the external bioimpedance system 80 or an internal bioimpedance system comprising at least two electrodes of the IMD 20. Injecting a current between any two electrodes for measurements of a voltage at another electrode can be used to determine a position of the electrode.

The electrodes of the leads 28a-28c can be positioned for pacing, defibrillation, sensing, and other appropriate purposes. Although any of the leads can be used for determining position information, it will be understood that the leads 28a-28d can include any appropriate number of electrodes to be used substantially only for position determination. For example, the lead 28d can include a tip electrode 34d and any appropriate number of intermediate electrode rings, such as three intermediate electrodes 36d', 36d", and 36d'". The lead 28d can be positioned along or attached to a wall of the heart 42 to provide plural points for position information. These multiple points can provide a substantially detailed view of a particular portion of the heart 42, such as a wall of the heart, when used to sense a position of the multiple electrodes 36d'-36d'" and 34d. It will be further understood that the multiple lead electrodes can be positioned at any appropriate distance along the lead 28d and can even be passed through more than one chamber of the heart 42 to illustrate relative motion of different portions of the heart 42.

When using the electrodes of the leads 28a-28d, it can be selected to calibrate the position information or the voltages generated relative to the electrodes of the IMD 20. The calibration can include determining the position between any two electrodes having a known position. For example, on the lead 28a, the tip 34a is generally at a fixed position relative to the ring electrode 36a. Accordingly, a determination of a position of each of the two electrodes 34a, 36a and this can be used to calibrate the position system. In addition, it will be understood that when the patch electrodes 82a-86d are positioned on the patient 40, the patch electrodes can be of appropriate sizes to inject the appropriate currents in the patient 40. In addition, the patch electrodes can be sized to provide an increase in a signal-to-noise ratio and decrease distortion generated by injecting a current into the patient 40.

The electrodes of the leads 28a-28d can be used to measure the positions of electrodes associated with each of the leads. The information can be transmitted, either as specific position information or as raw voltage data, to the external programmer 60 or the external bioimpedance system 80 for processing of position information. When the various leads are positioned in the right atrium, right ventricle, and the left ventricle, the leads can generally include electrodes that are substantially fixedly implanted into heart wall tissue in the various chambers. This also positions multiple electrodes within the various chambers so that multiple positions, regarding the various chambers, can be determined using the leads 28a-28d. The information relating to the positions of the leads 28a-28d can be used to identify various anatomical information, such as diseased regions of the heart, stroke volume, volume change and information relating to the various chambers of the heart 42, and other appropriate information. Various examples of information that can be determined using positions of various anatomical features is discussed in U.S. Patent Application Publication No. 2008/0132800 published on Jun. 5, 2008, incorporated herein by reference.

The electrodes positioned in the right ventricle can be used to determine an end diastolic dimension of the right ventricle. The end diastolic dimension can be proportional to a myocardial stretch and chamber volume. As is understood, the end diastolic ventricle or volume is an accepted index of ventricular preload which can be determinant of cardiac performance.

In addition, various leads can be positioned to determine thickness dimensions of a wall of the heart 42. As discussed above, an electrode can be positioned in the right ventricle and in the left ventricle. Accordingly, a thickness of the wall between the two ventricles can be measured instantaneously and over time. Thickening of the wall, generally referred to as hypertrophy, can be associated with hypertension and diastolic dysfunction. A thinning of the wall can be related to ischemia or dilated cardiomyophy. In addition, as discussed above, multiple position measurements can be taken during a single cardiac cycle or over multiple cardiac cycles and can be compared to similar positions within the single cardiac cycle. Therefore, a change in wall thickness can be measured over a cycle of the heart 42 for possible measuring or diagnosis of various cardiac diseases, such as ischemia which can be an indication of regional dyskinesis.

Regardless of the information determinations or calculations based upon the measured positions of the various electrodes, it will be understood that the positions of the various electrodes can be measured using either the external bioimpedance system 80 or an internal bioimpedance system (i.e., using the current source 130 within the IMD 20). Accordingly, a substantially continuous measurement of the positions of the electrodes can be made without requiring the patient 40 to be positioned relative to the external bioimpedance system 80 to determine the positions of the various electrodes. Accordingly, information can be recorded and saved in the P&M module 102 for transmission at a selected time. Additionally, the information saved within the P&M module 102 can be used to determine various pacing and defibrillation treatments of the IMD 20.

The information of the position of the electrodes acquired can be used to alter the programming of the IMD 20. The alteration of the programming of the IMD 20 can be done with the external programmer 60, after analysis of the position information, or done substantially in real time by the IMD 20, including the processor 102. For example, the IMD processor 102 can include instructions that can be executed to alter the programming, including pacing, of the IMD based upon position information of the various electrodes. The positions of electrodes can be determined using the current source 130 or any appropriate current source to determine positions of the electrodes. The IMD 20 can be used to alter the programming, including the pacing, of the IMD 20 without an external programmer. Accordingly, the positions of the electrodes can be used in substantially real time as a part of the treatment provided by the IMD 20.

Further areas of applicability of the present teachings will become apparent from the detailed description provided above. It should be understood that the detailed description and specific examples, while indicating various embodiments, are intended for purposes of illustration only and are not intended to limit the scope of the teachings.

What is claimed is:

1. A system to determine a location of an electrode within a volume, comprising:
   a medical device sized and shaped to be positioned by implantation and contained within the volume, the medical device including:
   a lead having a first implantable electrode;
   an implantable case containing an electronics system operable to receive a signal from the first implantable electrode, wherein the first implantable electrode is operable to move based on contact with a surface within the volume and relative to the implantable medical device;
   a connector extending from the lead to be connected to the electronics system; and
   a current injecting system operable to inject a current into the volume between a first injecting electrode and a second injecting electrode;
   wherein the first implantable electrode is operable to sense a voltage at a location due at least in part to the current injected into the volume.

2. The system of claim 1, wherein the current injecting system includes:
   a generator positioned exterior to the volume;
   wherein the generator is operable to deliver the current into the volume with the first injecting electrode and the second injecting electrode;
   wherein the first implantable electrode of the lead is operable to sense a voltage within the volume.

3. The system of claim 2, further comprising:
a third injecting electrode, a fourth injecting electrode, a fifth injecting electrode, and a sixth injecting electrode;
wherein two of each of the first, second, third, fourth, fifth and sixth injecting electrodes are paired to define three axes in the volume;
wherein the generator is operable to determine a period for injecting a current into the volume between each of the pairs of the injecting electrodes.

4. The system of claim 3, wherein the injected current has a frequency of about 1 kHz to about 10 kHz;
wherein the generator is operable to inject a current between the respective pairs of the injecting electrodes for about 10 cycles to about 200 cycles;
wherein after the selected number of cycles a current is injected with a different pair of the injecting electrodes from the previous pair of injecting electrodes.

5. The system of claim 3, further comprising:
a null period where no current is injected by the generator;
wherein the null period is operable to synchronize the current injecting system and the implantable medical device.

6. The system of claim 1, wherein the current injecting system includes:
a current source contained with the implantable medical device;
a second implantable electrode and a third implantable electrode;
wherein the third implantable electrode is a case of the implantable medical device;
wherein the current source is operable to inject a current using the first injecting electrode and the second injecting electrode selected from at least two of the first implantable electrode, the second implantable electrode, and the third implantable electrode;
wherein at least one of the first implantable electrode, the second implantable electrode, and the third implantable electrode is operable to sense a voltage due at least in part to the injected current.

7. The system of claim 6, wherein the implantable medical device further includes a processor operable to execute instructions to determine at least a relative position of a first sensed voltage and a second sensed voltage of at least one of the first implantable electrode, the second implantable electrode and the third implantable electrode due to the injected current.

8. The system of claim 7, wherein the processor is further operable to execute instructions to determine a pacing signal generated by the implantable medical device.

9. The system of claim 2, wherein the implantable medical device further includes an internal telemetry system;
wherein the internal telemetry system is operable to synchronize the signal received from the electrode and the current generated into the volume with the generator.

10. The system of claim 1, wherein the implantable medical device further includes:
a pacing and sensing module having an amplifier module through which a signal is transmitted and amplified from the first implantable electrode.

11. The system of claim 10,
wherein the signal from the amplifier module is transmitted to at least an impedance/position signal detection system and one of an electrogram filter, a myocardial infarction detection system, a sensing system for timing and rhythm detection, and an evoked response detection system.

12. The system of claim 10, wherein the implantable medical device further includes:
a filter having a band pass range of at least the injected current frequency.

13. The system of claim 12, wherein the band pass range is about 25 kHz to about 35 kHz.

14. The system of claim 11, wherein the implantable medical device includes a processor that undersamples the signal from the impedance/position signal detection system with intentional aliasing.

15. The system of claim 14, wherein the undersampled signal is operable to transmitted from the implantable medical device that includes substantially necessary information at a selected current drain.

16. The system of claim 14, wherein the processor is further operable to transform the undersampled signal in a selected frequency domain to identify three signal components;
wherein the signals are measured over time to determined information regarding the position of the electrodes.

17. The system of claim 14, wherein the processor is further operable to determine the position information of the first implantable electrode.

18. A system to measure a position of a surface of a portion of an anatomy, comprising:
a medical device sized to be implanted with the anatomy, including:
a lead including a first electrode fixed to a surface of the anatomy;
a position sensing system operable to sense a voltage at the first electrode at least a first time and a second time to generate a first sensed voltage signal and a second sensed voltage signal with the first electrode; and
a processor operable to compare a first sensed voltage and a second sensed voltage at the first electrode; and
a current injecting system operable to inject a current into the anatomical system to generate the voltage sensed by the first electrode;
wherein the processor undersamples the first sensed voltage signal and the second sensed voltage signal from the position sensing system with intentional aliasing.

19. The system of claim 18, further comprising a power source having a finite power supply.

20. The system of claim 19, further comprising:
a telemetry system wherein the undersampled signal is operable to transmitted from the medical device that includes substantially necessary information regarding a position of the first electrode at a selected current drain from the finite power supply.

21. The system of claim 20, further comprising:
a processor system having a second processor positioned exterior to the anatomy;
wherein the second processor is operable to transform the undersampled signal in a selected frequency domain to identify three signal components;
wherein the signals are measured over time to determine information regarding a position of the first electrode.

22. The system of claim 19, wherein the processor is operable to transform the undersampled signal in a selected frequency domain to identify three signal components;
wherein the signals are measured over time to determined information regarding the position of the electrodes.

23. The system of claim 19, wherein the processor is further operable to determine a position information of the first electrode.

24. The system of claim 19,
wherein the current injecting system is included in the medical device and the injected current is powered by the power source;
wherein the implantable medical device further includes:
a second electrode and a third electrode;
wherein the current injecting system is operable to use the power source as a current source system to inject a current between at least the first electrode and the second electrode;
wherein the position sensing system is operable to sense a voltage with at least the third electrode.

25. The system of claim 24,
wherein at least the first electrode is implanted within a surface of a heart in the anatomical system;
wherein the first sensed voltage signal and the second sensed voltage signal is operable by the processor to determine a position of at least the surface of a wall of the heart at least two times;
wherein the processor is operable to execute instructions to determine a change in position of the surface of the wall of the heart between the first time and the second time.

26. The system of claim 25, wherein the change in position is determined to be at least one of a heart wall thickness, a left ventricle volume, a left ventricle dimension, a right ventricle volume, a right ventricle dimension, a stoke volume, or combinations thereof.

27. A system to determine a location of an electrode with a volume, comprising:
a medical device sized to be positioned and contained within the volume, including:
an implantable case;
a lead connected to a connector associated with the implantable case having a first implantable electrode, wherein the first implantable electrode is operable to contact and move with a surface within the volume; and
a processor positioned within the implantable case and operable to execute a first set of instructions when a signal from the lead is received to affect the volume in a first manner; and
a current injecting system operable to inject a current into the volume between a first injecting electrode and a second injecting electrode and the first implantable electrode is operable to sense a voltage at a location due at least in part to the injected current;
wherein the processor is operable to change the first set of instructions based upon the sensed voltage to affect the volume in a second manner different from the first manner.

28. The system of claim 27, wherein the current injecting system includes three pairs of injecting electrodes that are operable to define three substantially orthogonal axes of current within the volume;
wherein the processor is operable to undersample a signal based the sensed voltage to produce an undersampled signal; and
wherein the implantable medical device further includes a telemetry system operable to transmit the undersampled signal that relates to the voltage sensed at the location.

29. The system of claim 28, wherein the processor is operable to execute instructions to determine a position of the first implantable electrode based at least in part on the voltage sensed at the location;
wherein the determined position can be transmitted from the implantable medical device.

30. The system of claim 29, further comprising:
an external processor system;
wherein the external processor system is operable to receive the transmitted determined position;
wherein the external processor system is operable to determine a condition of an anatomical feature within the volume based upon the transmitted determined position.

31. The system of claim 30, further comprising:
a second implantable electrode;
wherein the first implantable electrode is operable to sense a voltage at a first location and a second implantable electrode is operable to sense a voltage at a second location;
wherein at least one of the processor or the external processor system is operable to determine a dimension between the first implantable electrode and the second implantable electrode at the respective locations.

32. The system of claim 31, wherein the dimension is determined to be at least one of a heart wall thickness, a left ventricle volume, a left ventricle dimension, a right ventricle volume, a right ventricle dimension, a stoke volume, or combinations thereof.

33. A method of measuring movement of an electrode within a volume, comprising:
providing an implantable device;
implanting a lead extending from the implantable device into a surface within the volume, the lead having a first electrode;
injecting a current in the volume;
sensing a voltage in the volume with the first electrode;
sending a sensed voltage signal based on the sensed voltage to an electronics system of the implantable device; and
undersampling the sent sensed voltage signal.

34. The method of claim 33, wherein sensing a voltage includes:
sensing a first voltage at a first time and sensing a second voltage at a second time;
determining a first position of the first electrode with the first sensed voltage; and
determining a second position of the first electrode with the second sensed voltage.

35. The method of claim 34, further comprising:
implanting the first electrode in a surface;
determining a first position of the surface with the determined first position of the first electrode; and
determining a second position of the surface with the determined second position of the first electrode.

36. The method of claim 34, further comprising:
providing a processor in the implantable device;
providing a pacing system operable to deliver a pacing signal based upon first instructions executed by the processor; and
executing second instructions with the processor based upon the determined first position and the determined second position to alter the pacing signal.

37. The method of claim 34, further comprising:
placing a second electrode;
determining a third position of the second electrode; and
determining a distance between at least one of the determined first position and the determined second position and the determined third position.

38. The method of claim 37, further comprising:
implanting a second lead having the second electrode.

39. The method of claim 37, wherein the distance between one of the first position, the second position, or the third position is a thickness of an anatomical structure.

40. The method of claim 34, further comprising:
transmitting the undersampled signal that includes substantially necessary information at a selected current drain on a finite power supply to an external processor system; and
determining an anatomical definition based upon the transmitted undersampled signal.

41. The method of claim 33, further comprising:
generating the current to be injected into the volume with a generator that is external to the volume; and
synchronizing the external generation of the current from the generator with the sensing of the voltage with the first electrode.

42. The method of claim 41, wherein synchronizing the external generation includes sending a synchronization signal between the external generator and the provided implantable medical device or sensing a null voltage period in a pattern of generating the current.

43. A system to measure a position of a surface of a portion of an anatomy, comprising:
an implantable medical device including:
a lead including a first electrode;
a position sensing system operable to sense a voltage at the first electrode, the position sensing includes at least one of an electrogram filter, a myocardial infarction detection system, a sensing system for timing and rhythm detection, and an evoked response detection system;
a first processor operable to compare a first sensed voltage and a second sensed voltage at the first electrode;
a power source having a finite power supply; and
a first telemetry system operable to transmit and receive information regarding at least the first electrode; and
a current injecting system operable to inject a current into the anatomy to generate the voltage sensed by the first electrode, including:
a first pair of injecting electrodes and a second pair of injecting electrodes;
a current source system operable to inject a current between the first pair of injecting electrodes and the second pair of injecting electrodes; and
a second telemetry system operable to communicate with the first telemetry system;
wherein the first processor undersamples a signal from the first electrode to include intentional aliasing, wherein the undersampled signal is operable to be transmitted with the first telemetry system from the implantable medical device to the second telemetry system of the current injecting system, wherein the undersampled signal includes substantially all necessary information and is transmitted at a selected current drain from the finite power supply;
wherein a second processor of the current injecting system is operable to transform the undersampled signal in a selected frequency domain to identify three signal components;
wherein the signals are measured over time to determine information regarding the position of the first electrode.

44. The system of claim 43, wherein the implantable medical device further includes:
a second electrode;
wherein a voltage at the first electrode is compared to a voltage sensed at the second electrode;
wherein the processor is operable to execute instructions to determine a relative position of the first electrode and the second electrode, to identify a dimension of the anatomy.

45. The system of claim 43, wherein at least one of the first pair of injecting electrodes and the second pair of injecting electrodes are implanted within the anatomy with the implantable medical device.

* * * * *